US011053349B2

(12) United States Patent
Kouwer et al.

(10) Patent No.: US 11,053,349 B2
(45) Date of Patent: Jul. 6, 2021

(54) BIOMIMETIC NETWORKS COMPRISING POLYISOCYANOPEPTIDE HYDROGELS

(71) Applicant: STICHTING KATHOLIEKE UNIVERSITEIT, Nijmegen (NL)

(72) Inventors: Paul Kouwer, Nijmegen (NL); Alan Edward Rowan, Nijmegen (NL); Daniël Schoenmakers, Nijmegen (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 84 days.

(21) Appl. No.: 16/466,366

(22) PCT Filed: Dec. 5, 2017

(86) PCT No.: PCT/EP2017/081561
§ 371 (c)(1),
(2) Date: Jun. 4, 2019

(87) PCT Pub. No.: WO2018/104324
PCT Pub. Date: Jun. 14, 2018

(65) Prior Publication Data
US 2020/0140604 A1   May 7, 2020

(30) Foreign Application Priority Data

Dec. 5, 2016 (EP) ..................................... 16202260

(51) Int. Cl.
*C08G 61/04* (2006.01)
*A61L 27/52* (2006.01)
(Continued)

(52) U.S. Cl.
CPC .............. *C08G 61/04* (2013.01); *A61L 27/52* (2013.01); *C08G 65/33324* (2013.01);
(Continued)

(58) Field of Classification Search
CPC .............. C08G 61/04; C08G 65/33324; C08G 2261/122; C08G 2261/135;
(Continued)

(56) References Cited

FOREIGN PATENT DOCUMENTS

| WO | 2011007012 A1 | 1/2011 |
| WO | 2015007771 A1 | 1/2015 |
| WO | 2017037293 A1 | 3/2017 |

OTHER PUBLICATIONS

Das et al., Nature Materials | vol. 15 | Mar. 2016 , p. 318-327|.*
(Continued)

*Primary Examiner* — Shane Fang
(74) *Attorney, Agent, or Firm* — Hudak, Shunk & Farine Co. LPA (57) ABSTRACT

A polymer hydrogel having a polymer formed by the cross-linking reaction of a polymeric unit A according to formula (I), (Continued)

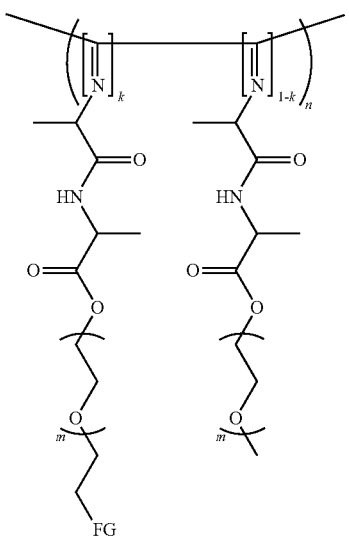

polymer A with a crosslinking unit B according to formula (II)

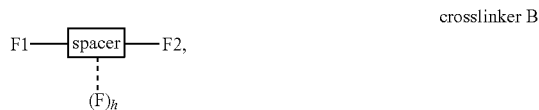

crosslinker B and water, wherein n=100-10,000, preferable 250-2500, more preferable 500-1500; m=independently 2-10, preferably 3 or 4; FG is a functional moiety that can be covalently coupled to the complementary functional moiety F1 or F2 of the crosslinking unit (B); k=0.01-0.05; h=0, 1 or 2; the spacer is an organic moiety, having a main chain comprising at least two functional moieties F1 and F2, wherein the length of the crosslinker in the extended conformation as determined by molecular modeling (including spacer and functional groups F1 and F2) is between 2.5 and 12 nm, or wherein the length is between 20 and 80 atoms.

19 Claims, 3 Drawing Sheets

(51) Int. Cl.
  *C08G 65/333* (2006.01)
  *C12N 5/00* (2006.01)
(52) U.S. Cl.
  CPC ...... *C12N 5/0068* (2013.01); *C08G 2261/122* (2013.01); *C08G 2261/135* (2013.01); *C08G 2261/1424* (2013.01); *C08G 2261/1432* (2013.01); *C08G 2261/332* (2013.01); *C08G 2261/76* (2013.01); *C12N 2533/20* (2013.01); *C12N 2533/30* (2013.01); *C12N 2533/76* (2013.01); *C12N 2537/10* (2013.01)
(58) Field of Classification Search
  CPC .... C08G 2261/1424; C08G 2261/1432; C08G 2261/332; C08G 2261/76; A61L 27/52; C12N 5/0068; C12N 2533/20; C12N 2533/30; C12N 2533/76; C12N 2537/10
  See application file for complete search history.

(56) References Cited

OTHER PUBLICATIONS

Jaspers, et al, Tuning Hydrogel Mechanics Using the Hofmeister Effect, Adv. Funct. Mater., 2015, vol. 25, No. 41, pp. 6503-6510, Wiley-VCH Verlag GmbH & Co.
Gardel, et al., Elastic Behavior of Cross-Linked and Bundled Actin Networks, Science, 2004, vol. 304, No. 5675, pp. 1301-1305.
Kouwer, et al., Responsive biomimetic networks from polyisocyanopeptide hydrogels, Nature, 2013, vol. 493, No. 7434, pp. 651-655.
Deshpande et al., DNA-Responsive Polyisocyanopeptide Hydrogels with Stress-Stiffening Capacity, Adv. Funct. Mater., 2016, vol. 26, No. 48, pp. 9075-9082, Wiley-VCH Verlag GmbH & Co.

* cited by examiner

BIOMIMETIC NETWORKS COMPRISING POLYISOCYANOPEPTIDE HYDROGELS

FIELD OF THE INVENTION

The invention relates to synthetic biomimetic networks comprising polyisocyano peptide hydrogels.

BACKGROUND OF THE INVENTION

Polyisocyanide hydrogels are known in the art. WO 2011/007012 discloses a hydrogel comprising oligo(alkylene glycol) functionalized polyisocyanopeptides. The polyisocyanopeptides are prepared by functionalizing an isocyanopeptide with oligo(alkylene glycol) side chains and subsequently polymerizing the oligo-alkylene glycol functionalized isocyanopeptides to polyisocyanopeptides (PIC). This PIC material is a fully synthetic strain-stiffening hydrogel with an architecture of polymer bundles. A solution of these polymers in water will show Lower Critical Solution Temperature (LCST) behavior; above the LCST a hydrogel is formed by formation of a branched network of entangled semi-flexible bundles, a consequence of entropic desolvation of the ethylene glycol moieties on the polymers. In the gel phase, the material mimics mechanical properties of natural materials, including strain-stiffening in the biologically reachable regime thanks to its architecture.

These polyisocyanopeptides can be used as a hydrogel for cultivating cells, which is disclosed in WO2015/007771.

SUMMARY OF THE INVENTION

For some applications, however, the ease of reversibility of mechanical properties may be a disadvantage. There is a need for a polymerized system, in which the mechanical properties can be tuned and kept constant for a longer time, without losing all special properties of the polyisocyanopeptides (PIC). Crosslinking of hydrogels and bundled hydrogels is a well-established method to stabilise the (mechanical) properties of a material in time. The present invention presents a method to selectively place the crosslinks inside the bundles of the PIC polymer and not randomly in the network, which is the commonly followed crosslinking approach. Using this method, the architecture of the porous, bundled network gel and the unique mechanical properties are retained. In common crosslinking approaches, the network architecture changes, which in turn changes the mechanical properties.

The inventors have found that a partial crosslinking of the bundles of PIC present in a hydrogel can stabilize the hydrogel, and reduce the temperature dependence after formation of the hydrogel. It is believed that the formation of crosslinks inside the bundled architecture is important in this process.

The invention therefore relates to a polymer hydrogel comprising a) a polymer formed by the crosslinking reaction of a polymeric unit A according to formula (I), polymer A with a crosslinking unit B according to formula (II)

crosslinker B b) and water, wherein $n=100$-10,000, preferable 250-2500, more preferable 500-1500;

$m=$independently 2-10, preferably 3 or 4;

FG is a functional moiety that can be covalently coupled to the complementary functional moiety F1 or F2 of the crosslinking unit (B);

$k=0.01$-0.05;

$h=0$, 1 or 2;

the spacer is an organic moiety, having a main chain comprising at least two functional moieties F1 and F2, wherein the length of the crosslinker in the extended conformation as determined by molecular modeling (including spacer and functional groups F1 and F2) is between 2.5 and 12 nm, or wherein the length is between 20 and 80 atoms.

The length of the crosslinking unit is calculated from the crosslink bond bridging F1 to a first polymeric unit, along the main chain of the spacer to the crosslink bond bridging F2 to a second polymeric unit, wherein the atoms of the main chain of the spacer and functional groups F1 and F2 are included, and wherein the shortest pathway is chosen, so that the minimum amount of atoms is being counted between the two crosslink bonds of the first and second polymeric chains.

The polymer can also be represented by formula (III), wherein n=100-10,000, preferable 250-2500, more preferable 500-1500; m=independently 2-10, preferably 3 or 4;

FG is a functional moiety that can be covalently coupled to the complementary functional moiety F1 or F2 coupled to a spacer of a crosslinking unit (B);

k=0.01-0.05;

l=0.002-0.05;

h=0, 1 or 2;

l/k is the conversion of FG moieties reacted with F1 and/or F2 moieties of the crosslinker unit B and ranges between 0.2 and 1;

the spacer is an organic moiety, having a main chain coupled to at least two functional moieties F1 and F2, wherein the length of the crosslinker in the extended conformation as determined by molecular modeling (including spacer and functional groups F1 and F2) is between 2.5 and 12 nm, or wherein the length is between 20 and 80 atoms.

Preferably the amount of polymer in the hydrogel ranges between 0.01 wt. % and 1 wt. %, more preferably between 0.02 wt. % and 0.5 wt. %.

The invention also relates to a process to prepare the polymer hydrogel, and to the use of the polymer hydrogel.

WO 2011/007012 mentions in general the possibility of crosslinking of the PIC polymer. It does not contain any examples of crosslinked materials, nor any details on how such crosslinking should be performed.

The inventors found that crosslinking according to the invention has a number of unexpected advantages, especially when crosslinkers are used having a specific size.

Figure 1:
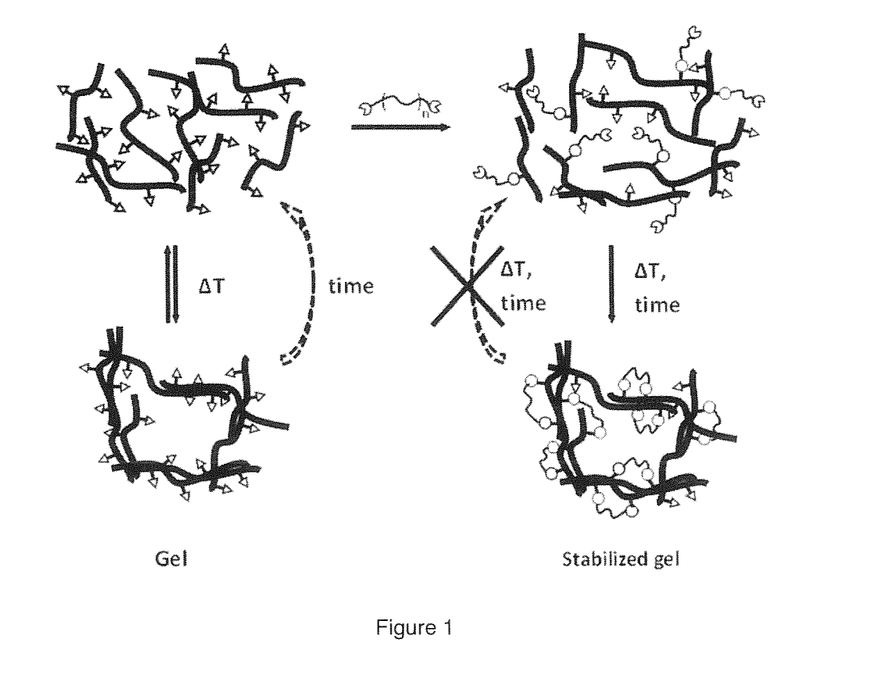
FIG. 1 shows the schematic formation of crosslinked PIC hydrogel.
Figure 2:
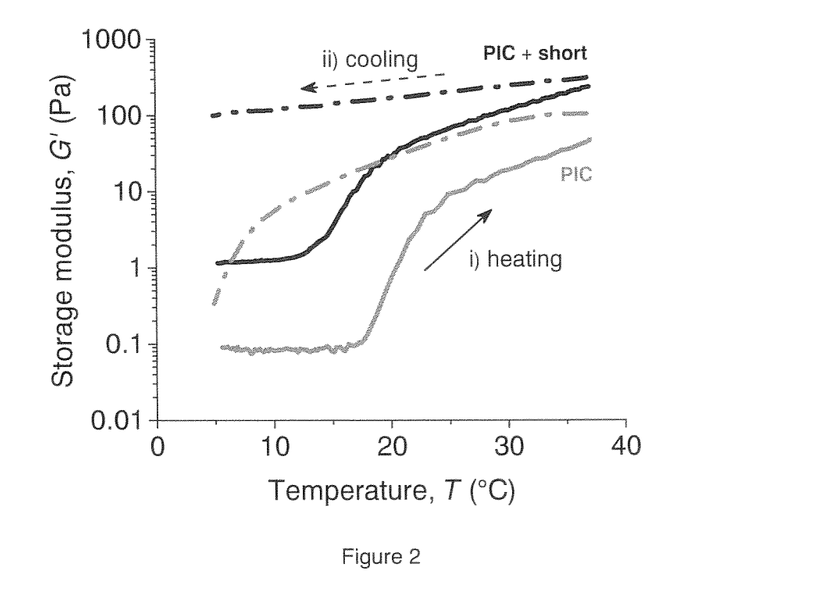
FIG. 2 shows the effect of formation of intra-bundular crosslinks at higher temperatures on the mechanical properties after cooling the crosslinked polymer hydrogel.
Figure 3:
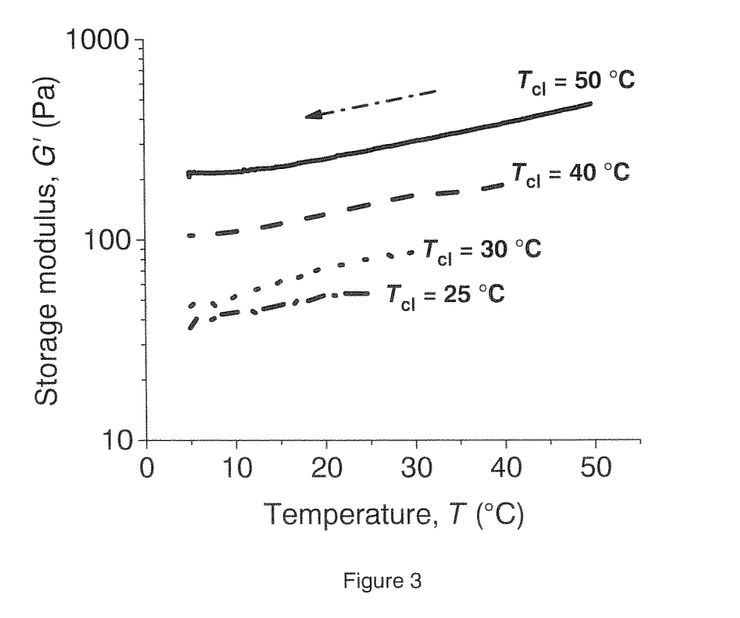
FIG. 3 shows the effect of crosslinking at different temperatures on the properties of the hydrogels as a function of temperature.
Figure 4:
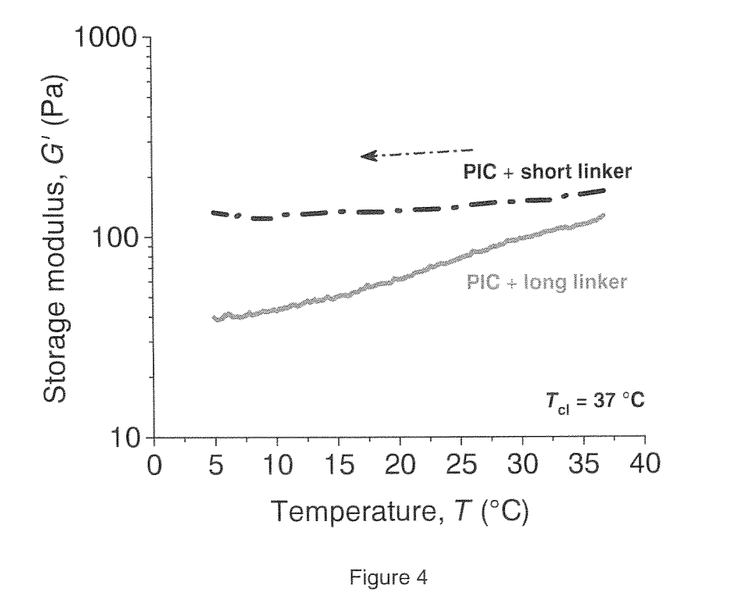
FIG. 4 shows the effect of using short (EO4) relative to long (EO26) spacers present in the crosslinking unit on the storage modulus.
Figure 5:
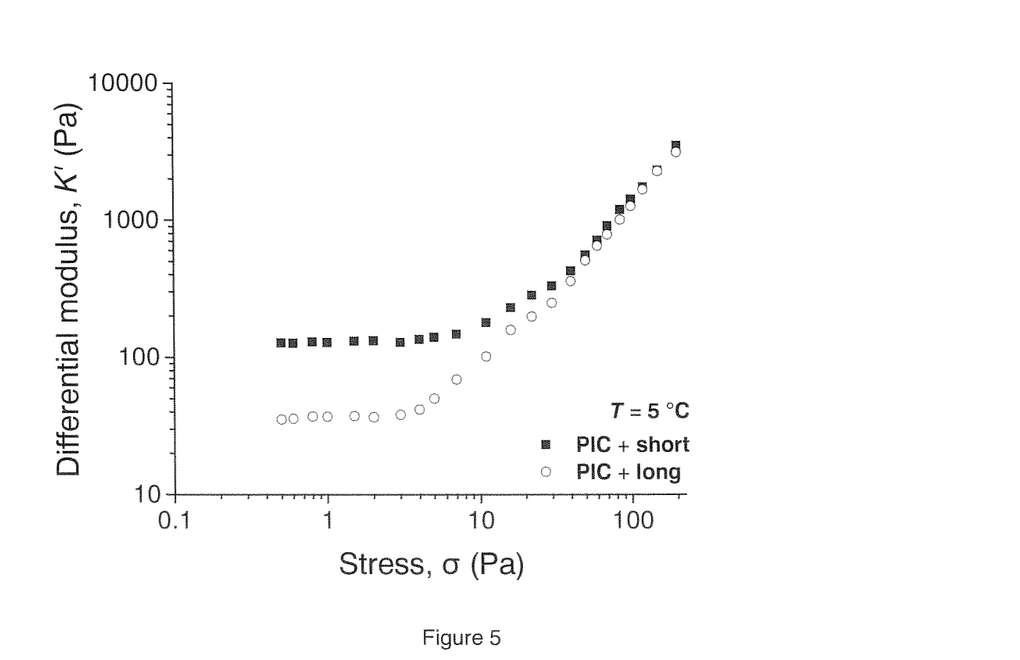
FIG. 5 shows the effect of using short (EO4) relative to long (EO26) spacers present in the crosslinking unit on the differential modulus.

In this patent application, the inventors present a method to conserve the mechanical properties and stability of a fully synthetic, biomimetic PIC hydrogel, without affecting the architecture. The inventors designed a method to crosslink PIC polymers in a controlled way, aiming for intra- rather than inter-bundular crosslinks so that the architecture is not changed but only stabilized. This way, the inventors are able to create a biomimetic network with the desired mechanical properties, freeze the architecture and keep these properties over a large temperature regime (see also FIGS. 1-3).

DETAILED DESCRIPTION OF THE INVENTION

The polymer hydrogel according to the present invention comprises a polymer according to formula (III), (III)

wherein n=100-10,000, preferable 250-2500, more preferable 500-1500;

m=independently 2-10, preferably 3 or 4;

FG is a functional moiety that can be covalently coupled to the complementary functional moiety F1 or F2 coupled to a spacer of a crosslinking unit (B);

k=0.01-0.05;

l=0.002-0.05;

h=0, 1 or 2;

l/k is the conversion of FG moieties reacted with F1 and/or F2 moieties of the crosslinker unit B and ranges between 0.2 and 1;

the spacer is an organic moiety, having a main chain coupled to at least two functional moieties F1 and F2, wherein the length of the crosslinker in the extended conformation as determined by molecular modeling (including spacer and functional groups F1 and F2) is between 2.5 and 12 nm, or wherein the length is between 20 and 80 atoms.

The length of the crosslinker unit in the extended conformation as determined by molecular modeling (including functional groups F1 and F2 and the spacer), ranges between 2.5 and 12 nm.

The length can alternatively be expressed as the number of atoms of the crosslink unit bridging the two polymeric chains. The number of atoms preferably ranges between 20 and 80 atoms. The number of atoms is the minimum atoms that can be counted between the crosslink bonds of the first and the second polymeric unit.

The polymer is a branched or crosslinked structure comprising a first polyisocyanopeptide polymer chain coupled through a FG-F1 bridge to a second polyisocyanopeptide polymer chain through a FG-F2 bridge, and optionally coupled to additional polymeric units through F. The crosslinking unit has a specific size, in order to provide predominantly intrabundular crosslinks. Other types of crosslinks like intramolecular (within one single polymer chain), or interbundular (between adjacent bundles of PIC polymer chains) are not effective in providing the polymer and hydrogel according to the present invention.

Preferably the polymer in the hydrogel contains the reaction product of a difunctional crosslinker (having functional groups F1 and F2) and the polymeric monomer unit (A) and has the formula IV (IV)

wherein n, k, m, F1, F2, FG, spacer are as defined before.

In one embodiment the polymer in the hydrogel contains the reaction product of a difunctional crosslinker (having functional groups F1 and F2) and the polymeric monomer unit (A) and has the formula V (V)

wherein n, k, m, F1, F2, FG, spacer are as defined before.

The polymer hydrogel is formed by the crosslinking reaction of a polymeric unit A according to formula (I)

polymer A with a crosslinking unit B according to formula (II)

crosslinker B

The polymeric units A can be formed by copolymerizing a first comonomer of an oligo(ethylene glycol) functionalized isocyanopeptide grafted with a functional group FG and a second comonomer of a non-grafted oligo(ethylene glycol) functionalized isocyanopeptide.

The number of ethylene glycol units (m) ranges independently between 2 and 10, preferably the number of ethylene glycol units is 3 or 4, most preferably 3.

The functional group FG of the polymeric unit (A) may react with a functional group F1, F2 or F on the crosslinking unit, thereby forming a covalent bond, or crosslinking bond.

Figure 6:
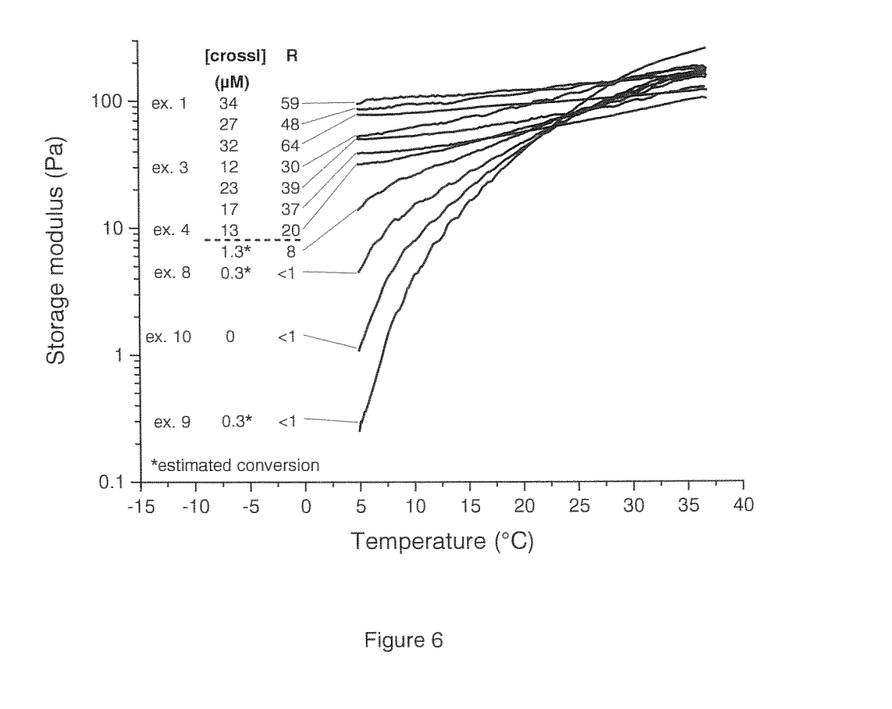
FIG. 6 shows the thermal stability of the gel as a function of the crosslink concentration [crossl] given in μM. The stability is quantified by $R=100\% \times G'_5/G'_{37}$.

In many cases, not all functional group in the polymer (FG) or on the crosslinker (F1, F2) react, which means that the conversion of FG groups is not 100%, and l/k<1. This can be readily tuned by the ratio between the two different groups. At equal concentrations, the conversion approaches 90%. At a low concentration of crosslinker (B), the conversion of FG will be low, while at a high concentration of crosslinker (B), the conversion of FG groups will be high, but the crosslinking efficiency may still be low, since the crosslinker unit is present in excess and does not form desired crosslinks. The conversion is expressed at the ratio of converted functional groups (FG) on the polymer, l, against the originally present number of functional groups on the polymer, k: conversion=l/k. The total crosslink density is calculated as the concentration functional groups in the polymer [FG] times the square of the conversion: [x-links]=[FG]*(l/k)$^2$, and should be between 20-100 μM, see FIG. 6.

A crosslink density in the range between 20-100 μM can practically been achieved by providing a hydrogel containing polymer A having a [FG] between 20 and 200 μM, preferably between 50 and 150 μM, to be reacted with the crosslinker B. Preferably the molar ratio between [FG] and [F] ranges between 0.5:1 and 2:1, more preferably between 0.7:1 and 1.5:1.

The size of the polymer unit (A) can vary: n is typically ranging between 100 and 10000, preferably between 250 and 2500, more preferably between 500 and 1500.

The ratio of the first monomer unit having the functional group FG and the second monomer unit having no functional group FG is also important; k typically ranges between 0.01 and 0.05. Preferably k ranges between 0.02 and 0.04. This means that the molar amount of first monomer ranges between 1 and 5 mol % relative to the total of the polymeric unit, preferably between 2 and 4 mol %.

A too high amount of first monomer units having a functional group FG, may decrease the water solubility of the polymeric unit, thereby decreasing the usability to prepare gels.

When the amount of functional groups FG is too low, the crosslink density will be too low and a stabilizing effect at low temperatures cannot occur to a satisfactory level. When the amount of functional groups FG is too high, many of the crosslinks will be intramolecular and will not contribute to the stabilization of the network.

The polymer hydrogel according to the invention is formed by the reaction of polymeric units (A) having functional groups FG with a crosslinking unit (B) having functional groups that can react with the functional groups FG. The crosslinking unit (B) comprises a spacer and at least two functional groups F1 and F2 that can react with functional groups FG of the polymeric unit (A). It is possible that the crosslinking unit has more than two functional groups capable of reacting with the functional groups FG of the polymeric unit, for example 3 functional groups, or 4 functional groups. Preferably the crosslinking unit has 2 functional groups.

In a preferred embodiment F1 and F2 are the same functional groups.

Examples of suitable functional groups F1, F2 and functional groups FG that can give covalently couplings are: alkyne-azide coupling, dibenzocyclooctyne-azide coupling, bicyclo[6.1.0]non-4-yne-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages, tetrazine-trans-cyclooctene coupling and NHS-ester (N-hydroxysuccinimide ester)-amine coupling.

Preferred couplings are based on azide-alkene and/or azide-alkyn coupling such as dibenzocyclooctyne-azide coupling, bicyclo[6.1.0]non-4-yne—based-azide couplings.

Preferred examples of functional groups F1 and F2 of the crosslinking unit are selected from and and their derivatives.

The crosslinking unit comprises a spacer between the two or more functional groups F1 and F2. The length of the crosslinking unit (including the spacer and two functional groups F1 and F2) is between 2.5 and 12 nm. Alternatively, the length of the crosslinking unit can be expressed as the minimum number of atoms between the crosslinks bonds connecting FG with either F1 or F2. Preferably the number of atoms bridging the first and second polymer chain is between 20 and 80 atoms, or between 25 and 60 atoms.

The length of the crosslinking unit is calculated from the crosslink bond bridging F1 to the first polymeric unit, along the main chain of the spacer to the crosslink bond bridging F2 to the second polymeric unit, wherein the atoms of the main chain of the spacer and functional groups F1 and F2 are included, and wherein the shortest pathway is chosen, so that the minimum amount of atoms is being counted between the two crosslink bonds of the first and second polymeric chains.

Preferably the length of the crosslinking unit ranges between 3 and 9 nm, or between 3.5 and 6 nm.

Examples of suitable spacers comprise polyethylene glycol units, having from 3 to 26 ethylene glycol units, preferably between 4 and 14, or between 4 and 10 ethylene glycol units. In case the spacer comprises ethylene glycol units (EG) the relation between length (nm) and number of EG units is as follows: A short spacer having 4 EG units has a length of approximately 2 nm. A spacer having 14 EG units, has a length of approximately 5 nm, while a long spacer having 26 EG units has a length of 9 nm.

Other examples are spacers comprising short peptide sequences, that may be cleavable metalloproteinase (MMP) including MMP-1 and MMP-2, for instance, but not limited to the peptides VPMSMRG, VPMSMRGG, RPMSMR, IPESLRAG, IPVSLRSG, VPLSLYSG, VPMSMR, PAYYTA, GPQGIWGQ, SGESPAYYTA, GPQGIAGQ, RPFSMIMG, VPLSLTMG, YAAPVRGG, GTAGLIGQ or GDQGIAGF, more preferably VPMSMRG, VPMSMRGG, RPMSMR, IPESLRAG, IPVSLRSG, VPLSLYSG, VPMSMR and KVPMSMRGK. Herein, V=Valine; P=Proline; M=Methionine; S=Serine; R=Arginine; G=Glycine; I=Isoleucine; E=Glutamic Acid; L=Leucine; A=Alanine; Y=Tyrosine; Q=Glutamine; K=lysine and F=Phenylalanine.

It is also possible to use photo cleavable crosslinks, wherein the spacer contains a dye that is able to cleave the spacer on irradiation with the appropriate wavelength, for instance coumarin-based dyes Φ1 and Φ2 and derivatives, that react upon exposure to visible or near IR light, respectively, and as a result, cleave the spacer.

The spacers containing short peptide sequences or photocleavable crosslinks may also comprise ethylene oxide monomeric units to increase the solubility in water.

A preferred embodiment of the invention uses a precursor of the crosslinking unit which is a molecule according to formula IV

| Example | p | length crosslinker |
|---------|----|--------------------|
| 1 | 4 | 3.5 nm |
| 2 | 14 | 8 nm |
| 3 | 26 | 12 nm | wherein the length of the crosslinker is between 2.5 and 12 nm, preferred between 3.5 and 9 nm.

In another preferred embodiment, the crosslinker has a structure according to any one of

V

VI p = 0-10

VII p = 0-10

VIII p + q = 0-10 wherein the peptide is cleavable by a metalloproteinase (MMP). Peptides are preferably having the sequences as defined above.

In one embodiment a photocleavable crosslinker is being applied. Examples of photocleavable crosslinkers are:

IX

X p = 0-14 p = 0-14
Y = independently O or NH p + q = 0-14
Y = independently O or NH where Φ is a photocleavabe dye that, as a result of the photochemical reaction, cleaves the spacer, for instance:

Φ1 photocleavable dye 1: λ = 450 nm

Φ2 photocleavable dye 2: λ = 740 nm

The amount of water in the hydrogel ranges between 90 and 99.99 wt. % relative to the total of the hydrogel.

The hydrogel can contain other components in addition to water and the polymer, like for example cell culture media, cells, other solvents (like for example DMSO) and the like.

The polymer in the hydrogel can also contain other chains or branches in addition to the branches as defined by formula I and III. For example, the polymeric unit A can contain ligands, adhesion factors, growth factors, antibodies, peptides or other bioactive moieties as well as (fluorescent) dyes or any other functional organic molecule. The ratio of reacting functional groups is also relevant for the formation of the crosslinked network. Preferably the ratio of functional groups (F1+F2+(F)h) attached to the crosslinker to the amount of FG functional groups attached to the polymeric units ranges between 50 and 150 mol %, more preferably between 70 and 130 mol %, or between 80 and 120 mol %.

The polymer present in the hydrogel according to the invention is at least partially crosslinked. Due to the right size of the spacer, the crosslinker does not (substantially) form intra-molecular crosslinks. Rather the inventors believe that the crosslinks are mainly formed intra-bundular, thereby stabilizing the gel. The crosslinks are preferably not extended between different bundles of polymer chains (inter-bundular), since this would negatively impact the large pore size of the biomimetic gel and the modulus.

The crosslinking of the polymer stabilizes different mechanical properties, as a function of the temperature of reaction between the polymer and the crosslinker and the temperature of measurement (after the crosslinking reaction). First the hydrogel is brought to a certain temperature: the temperature of the uncrosslinked hydrogel determines a number of mechanical parameters. Change of the temperature will change these parameters rather quickly, since the parameters are temperature dependent.

Intra-bundular crosslinking of the hydrogel at a defined temperature will stabilize the parameters at that temperature, and makes the parameters less temperature dependent. See for example FIG. 1: in the left part of the figure, the behavior of the known PIC (uncrosslinked) shows a reversible bundle formation as a function of the temperature. At low temperature (for example at 5° C.), a dilute polymer solution is found. Upon warming up to for example 37° C., bundles of polymers are being formed which give the characteristic mechanical properties of these polymers. This behavior is reversible for non-crosslinked PIC hydrogels. In the right part of FIG. 1, it is shown that the addition of a crosslinker will generate a crosslinked structure, but mainly after the bundles have been formed. By the crosslinking reaction, the reversibility of this process is stopped.

The formation of bundles is temperature dependent. When a hydrogel of a first sample is made at a first temperature and subsequently crosslinked, a hydrogel will be obtained having properties at a level determined by the first temperature. When an uncrosslinked hydrogel of a second sample is brought to a second temperature, which is different from the first temperature, a second hydrogel will be obtained having different properties compared to the first sample. Crosslinking will generate two hydrogels which will have different properties at the same temperature, see FIGS. 2 and 3.

Preferably, the temperature of hydrogel formation ranges between 20 and 50° C., more preferably between 22 and 40° C.

The crosslink density can be determined by two independent methods: chemical analysis and mechanical analysis.

Calculation of the amount of crosslinks can be done in a theoretical way, by assuming that only intra-bundular crosslinks are being formed. In this case the amount of functional groups FG in the polymeric units (A) are known from the synthesis of the polymer, and the amount of crosslinks can be calculated depending on the concentration of functional groups FG in polymer [FG], the concentration of functional groups [F1]+[F2]+[F] in the crosslinking agent and the conversion C of the functional groups FG, which can be determined with UV-vis absorption spectroscopy. This gives a theoretical crosslink density (moles of crosslinks per volume) $\rho_{cl}=[FG] \cdot C^2$. In samples with high crosslink density, i.e. $\rho_{cl}>20$ μM, the mechanical properties of the sample will be stable.

Also a mechanical analysis can be performed. Mechanical analysis is based on the decrease in macroscopic stiffness on cooling the hydrogel. The stiffness of the samples with low crosslink density and with crosslinks with too high spacer lengths will decrease when bundles loosening occurs on cooling. This method yields the percentage of stiffness remaining at 5° C., $G'_5$, as compared to the stiffness at the 37° C., $G'_{37}$:

$$R=100\% \times G'_5/G'_{37}.$$

At high crosslinking densities, percentage R will be high: above 40%.

At low crosslinking densities, the R will be low; at values R<10%, the degree of crosslinking is so low that the gel is nearly fully disintegrated at low temperatures (for example between 0 and 5° C.).

At intermediate values 10%<R<40%, the bundled architecture of the gel is maintained, but the bundles are loose and the mechanical properties have reduced considerably. In these gels, however, the nonlinear mechanical properties of the gels are maintained.

Preferably R is at least 20%, more preferably at least 30%. Most preferably, R is at least 40%.

According to one aspect, the present invention provides a process for making an oligo(ethylene glycol) functionalized co-polyisocyanopeptide, wherein the process comprises the steps of:
i) copolymerizing
   a first comonomer of an oligo(ethylene glycol) functionalized isocyanopeptide grafted with a functional group FG and
   a second comonomer of a non-grafted oligo(ethylene glycol) functionalized isocyanopeptide,
   wherein the molar ratio between the first comonomer and the second comonomer is 1:100 and 1:20 to prepare a polymer (A);
ii) dissolving polymer (A) in water to a concentration between 0.01 and 1 wt. % polymer in water between 0 and 10° C. to prevent hydrogel formation;
iii) adding a crosslinking compound having a spacer unit and at least two functional groups $F=F1=F2=(F)_n$ capable of reacting with the functional group FG, wherein the functional group FG and the functional group F are chosen to react and form a coupling; wherein the coupling is independently selected from the group consisting of alkyne-azide coupling, dibenzocyclooctyne-azide coupling, oxanorbornadiene-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages, tetrazine-trans-cyclooctene and NHS-Ester (N-Hydroxysuccinimide ester)-amine coupling;
iv) bringing the hydrogel within 10 minutes to the desired crosslinking temperature for gel formation (fast) at temperatures above the LCST or gelation temperature and the reaction with a crosslinking compound (slower).

For efficient crosslinking, the formation of a hydrogel is needed: otherwise the concentration of functional groups FG is very low, and consequently the crosslinking reaction takes place slowly. Once the bundles have been formed, the local concentration of functional groups FG increases and the crosslinking reaction will start to run. It is preferred that the formation of gels is fast relative to the crosslinking reaction, so that first the gel formation can take place, with formation of the desired mechanical properties, followed by 'freezing' of the properties by the crosslinking reaction.

The temperature of reaction preferably ranges between 20 and 50° C., more preferably between 22 and 40° C.

The functional group FG and group F (this is F1, F2 and F) are chosen to react and form a coupling which may be any coupling mentioned in the above list. For example, in order to obtain an alkyne-azide coupling, the functional group FG may be alkyne and group F may be azide or the functional group FG may be azide and group F may be alkyne. The couplings mentioned in the above list are well-known to the skilled person and the formation of the couplings are found in textbooks. For example, $NH_2$—COOH coupling can be mediated via EDC.

Preferably, the coupling is an alkyne-azide coupling.

Polymerization

The oligo(ethylene glycol) isocyanopeptide monomer grafted with the functional group FG (first comonomer) and the oligo(ethylene glycol) isocyanopeptide monomers not grafted with the functional group FG (second comonomer) are mixed and subsequently copolymerized.

The copolymerization is preferably performed in the presence of an apolar solvent. Suitable apolar solvents may be selected from the group consisting of saturated hydrocarbon solvents and aromatic hydrocarbon solvents or mixtures thereof. Examples of apolar solvents are pentane, hexane, heptane, 2-methylbutane, 2-methylhexane, cyclohexane, and toluene, benzene xylenes or mixtures thereof. Preferably toluene is chosen for the polymerization process of oligo(ethylene glycol) isocyanopeptides where the oligo (ethylene glycol) part contains at least three ethylene glycol units.

Preferably the polymerization is carried out in the presence of a catalyst. The catalyst is preferably a nickel(II) salt. Example of Ni(II) salts are nickel(II) halides (e.g. nickel(II) chloride), nickel(II) perchlorate or tetrakis-(tertbutylisocyanide)nickel(II) perchlorate.

Other complexes and nickel salts might be used provided that they are soluble in the polymerization medium or initially dissolved in an adequate solvent which is miscible in the polymerization medium.

Preferably the monomer concentration is chosen above 30 mmol/L and the catalyst/monomer ratio chosen between 1/100 and 1/10 000. Lowering the amount of nickel(II) (catalyst/monomer ratio below 1/1000) permits the preparation of materials exhibiting a substantial degree of polymerization [mean DP>500], which is desired for subsequent application of the polymers as macro-hydrogelators.

In a representative example, a millimolar solution of monomer in a nonpolar organic solvent or mixture of solvents is added to a nickel (II) catalyst dissolved in a polar solvent in a molar ratio of 1:50 up to 1:100,000 catalyst to monomer. In a sealed environment the mixture is stirred for 2 to 72 hrs. Once completed, the reaction mixture is diluted with solvent and precipitated in diethylether or similar non-compatible organic solvents, giving the desired product.

The invention also relates to polymer hydrogels that are further substituted with ligands, adhesion factors, growth factors, antibodies, peptides or other bioactive moieties as well as (fluorescent) dyes or any other functional organic molecule.

The invention also relates to the use of the polymer hydrogels according to the invention, for example in tissue engineering and soft robotics.

The invention also relates to cell cultures comprising cells, cell culture medium and the hydrogel according to the present invention.

DETAILED DESCRIPTION OF THE INVENTION

Experimental

Materials: Toluene was distilled over sodium. Water was purified with a MilliPore MilliQ system, (mQ water 18.2 MΩ). Unless stated otherwise, all chemicals were obtained from commercial sources and used without further purification. If no further details are given the reaction was performed under ambient atmosphere and temperature. Column chromatography was performed using silica gel (0.060-0.200 mm) provided by Baker.

Synthesis of the Azide-Functionalized Isocyanide Ionomer

The azide-functionalized isocyanide monomer was synthesized following a modified literature procedure. The first and last step of the procedure were altered.

Synthesis of Tetraethylene Glycol p-Toluenesulfonate

Tetraethylene glycol (52.68 g, 271 mmol) was dissolved in 10 mL THF and the solution was cooled to 0° C. A solution of NaOH (1.81 g, 45.25 mmol) in 10 mL water was added and the mixture was stirred vigorously for 5 minutes. A solution of tosyl chloride (8.08 g, 42.4 mmol) in 70 mL THF was added drop wise. The reaction mixture was stirred for 2.5 h. Subsequently, the solution was poured onto ice water (200 mL) and 50 mL of dichloromethane (DCM) was added. The water layer was extracted 4 times with 100 mL of DCM. The combined organic layers were dried using anhydrous $NaSO_4$ and the solvents were removed in vacuo. The product was purified using flash chromatography ($SiO_2$, EtOAc) to yield 11.8525 g (80%) of a yellow oil.

Analysis: FT-IR ($cm^{-1}$, ATR) 3442 (O—H), 2870 (C—H), 1597 (N—H), 1453 (C—H), 1352 (S=O), 1175 (S=O), 1096 (C—O); $^1$H-NMR $\delta_H$ (300 MHz; $CDCl_3$; $Me_4Si$) 7.80 (dd, J=7.81 Hz, 2H, —$CH_{Ar}$—), 7.33 (d, J=7.35 Hz, 2H, —$CH_{Ar}$—S), 4.17 (m, 2H, O—$CH_2$—$CH_2$—), 3.65 (m, 16H, —$CH_2$—), 2.45 (s, 3H, —$CH_3$); $^{13}$C-NMR $\delta_C$ (75 MHz; $CDCl_3$; $Me_4Si$) 21.16 (1C, $CCH_3$), 61.0 (1C, COH), 68.13 (1C, COS), 69.0 (1C, $OCH_2$), 70.0, 70.1, 70.1, 70.2 (4C, $OCH_2$), 70.8, 72.0 (2C, $OCH_2$), 127.5 (2C, CHCCH), 129.5 (2C, CHCCH), 139.7 (1C, $CCH_3$), 144.5 (1C, CHCS).

Synthesis of (R)-2-(2-(2-(2-azidoethoxy)ethoxy) ethoxy)ethyl 2-((S)-2-isocyanopropanamido)propanoate (R)-2-(2-(2-(2-azidoethoxy)ethoxy)ethoxy)ethyl 2-((S)-2-formamidopropanamido)propanoate (640 mg, 1.64 mmol) was dissolved in 60 mL of freshly distilled DCM. To this solution, methyl N-(triethylammoniumsulfonyl)carbamate (Burgess reagent; 594 mg, 2.49 mmol) was added. The mixture was stirred at rt for 6 h until no starting material was observed on TLC. The solvents were removed in vacuo, and the product was purified using flash chromatography ($SiO_2$, 3:1 DCM:MeCN) to yield 0.436 g (72%) of a pale yellow oil.

Analysis: FT-IR ($cm^{-1}$, ATR) 3318 (N—H), 2875 (C—H), 2142 (C≡N), 2105 ($N_3$), 1744 (C=O), 1540 (N—H), 1453 (C—H), 1123 (C—O); $^1$H-NMR $\delta_H$ (300 Hz; $CDCl_3$; $Me_4Si$) 7.00 (bd, 1H, —NH—), 4.59 (m, 1H, —NHCH($CH_3$)C(O)O—), 4.32 (m, 3H, (—C(O)

OCH$_2$CH$_2$O—), —C≡NCH(CH3)C(O)NH—), 3.67 (m, 12H, —(OCH$_2$CH$_2$)$_3$), 3.39 (m, 2H, N$_3$CH$_2$—), 1.65 (d, J=7.2, 3H, C≡NCH(CH$_3$)C(O)—), 1.48 (d, J=7.2, 3H, C≡NCH(CH$_3$)C(O)—); $^{13}$C NMR δ$_C$ (75 MHz; CDCl$_3$; Me$_4$Si) 170.69 (1C, CH(CH$_3$)C(O)OCH$_2$), 165.72 (1C, CH(CH$_3$)C(O)NH), 70.69, 70.65, 70.61, 70.56, 70.02, 68.81 (1C, CH$_2$CH$_2$O), 50.66 (1C, CH$_2$N$_3$), 48.56 (C≡NCH), 19.66, 18.04 (1C, CH(CH3)CO); S (ESI) m/z [M+Na]$^+$ (C$_{15}$H$_{25}$N$_5$O$_6$Na), calcd 394.17; found 394.1.

Polymerization

The commercial methoxy-terminated isocyanide monomer was further purified by flash chromatography (SiO$_2$, 1:3 MeCN:DCM) before use. The purified monomer (250 mg, 0.79 mmol) and the azide functionalized isocyanide monomer (10.1 mg, 0.027 mmol) were dissolved in freshly distilled toluene (4 mL). Subsequently, 81.7 μL of a freshly prepared solution of 1 mM Ni(ClO$_4$)$_2$.6H$_2$O in freshly distilled toluene containing 10% EtOH was diluted to 1 mL using freshly distilled toluene. This catalyst dilution was added to the monomer solution. The resulting mixture was stirred for 72 h at rt. Afterwards, the reaction mixture was diluted with dichloromethane and the product was precipitated in di-isopropyl ether. This workup was repeated thrice. The product was yielded as 243.6 mg (94%) of a yellow solid.

FT-IR $v_{max}$ film (cm$^{-1}$): 3268, 2876, 1742, 1657, 1532, 1455, 1264, 1217, 1065, 729, 703. M$_v$=599 kDa, UV-Vis λ$_{max}$ (25° C., milliQ)=245 nm.

Synthesis of Long Crosslinker

4-Dimethylaminopyridine (DMAP, 0.5 mg, 4.4 μmol), DBCO-amine (38.1 mg, 138 μmol) and PEG(1000) bis-acetic acid (49.7 mg, 44 μmol) were dissolved in freshly distilled DCM (5 mL).

14<m<26

The reaction mixture was cooled to 0° C. 1-Ethyl-3-(3-dimethylaminopropyl)carbodiimide hydrochloride (EDC, 28 mg, 146 μmol) was added and the mixture was allowed to warm up to room temperature. The solution was stirred overnight at rt. Afterwards, the reaction mixture was diluted with DCM, and the organic layer was washed with water (3×50 mL) and brine (1×50 mL). The organic layer was dried with anhydrous Na$_2$SO$_4$ and the solvents were evaporated in vacuo. The product was dissolved in 1 mL of tetrahydrofuran (THF), filtered and the solvent was evaporated in vacuo. This procedure was repeated once. For further purification, the product was dissolved in a minimum amount of THF and precipitated in cold heptane. This procedure was repeated twice, after which the product was yielded as 59.7 mg (84%) of a yellow oil.

$^1$H-NMR (500 MHz, CDCl$_3$, ppm) δ: 7.70 (d, 2H, C$_{Ar}$H), 7.46-7.31 (m, 14H, C$_{Ar}$H), 7.13 (br t, 2H, NH), 5.16 (d, 2H, C$_3$H), 3.90 (q, 4H, C$_8$H$_2$), 3.80-3.60 (m, 88H, —O—CH$_2$—CH$_2$—, C$_3$H), 3.60-3.49 (m, 8H, —O—CH$_2$—CH$_2$—), 3.44-3.32 (m, 4H, C$_6$H$_2$), 2.55 (dt, 2H, C$_5$H), 2.02 (dt, 2H, C$_5$H). $^{13}$C-NMR (126 MHz, CDCl$_3$, ppm) δ: 171.56 (C$_4$), 169.79 (C$_7$), 151.11 (C$_{Ar}$), 148.07 (C$_{Ar}$), 132.16 (C$_{Ar}$), 129.09 (C$_{Ar}$), 128.58 (C$_{Ar}$), 128.29 (C$_{Ar}$), 128.23 (C$_{Ar}$), 127.73 (C$_{Ar}$), 127.18 (C$_{Ar}$), 125.53 (C$_{Ar}$), 123.07 (C$_{Ar}$), 122.55 (C$_{Ar}$), 114.80 (C$_1$), 107.74 (C$_2$), 70.86 (—CH$_2$—CH$_2$—O—), 70.56 (—CH$_2$—CH$_2$—O— and C$_8$), 70.27 (—CH$_2$—CH$_2$—O—), 55.45 (C$_3$), 34.78 (C$_5$, C$_6$). MALDI-TOF: m/z=1377.6179, 1421.6465, 1465.6640, 1509.6913, 1553.7158, 1597.7458, 1641.7732, 1685.8016, 1729.8202, 1773.8499, 1817.8627, 1861.8839 and 1905.8782 which corresponds to DBCO-(CH$_2$CH$_2$O)$_n$-DBCO+Na$^+$ (n=14-26) and 1569.6882, 1613.7091, 1657.7335 and 1701.7500 which corresponds to DBCO-(CH$_2$CH$_2$O)$_n$-DBCO+K$^+$ (n=17-20). FT-IR $v_{max}$ film (cm$^{-1}$): 3507 (N—H), 2870 (C—H), 1655 (C=O amide), 1535, 1466, 1449, 1398, 1325, 1250, 1206, 1101 (C—N), 949, 846, 729. UV-Vis λ$_{max}$ (25° C., milliQ)=290.5 nm. ε$_{290.5}$ (milliQ)=16430 L mol$^{-1}$·cm$^{-1}$.

Crosslinking Reaction

When Dibenzocyclooctyn (DBCO)-based crosslinkers are used, the conversion of the DBCO groups can be followed experimentally using UV-vis spectrosopy. To this end, the (decreasing) DBCO absorbance at λ=304 nm is traced during the crosslinking reaction. The concentration remaining DBCO groups can be calculated from the extinction coeffcient at λ=304 nm: ε$_{304}$=7610 L mol$^{-1}$ cm$^{-1}$.

Preparation of the Hydrogel from the Copolymer

A homogeneous solution of 2 mg mL$^{-1}$ polyisocyanide copolymer was prepared by dissolving the dry polymer in the appropriate amount of milliQ water over night at 4° C., and occasionally shaking. All polymer solutions were stored at −20° C. until further use.

Example 1

Preparing a Crosslinked Hydrogel

A solution of 2 mg mL$^{-1}$ of the commercially available short crosslinker in DMSO, or 2 mg mL$^{-1}$ of the long crosslinker in milliQ water, was prepared and diluted to the desired concentration using milliQ water. The concentrations were chosen such that the polymer and crosslinker solutions could be mixed in a 1:1 ratio to achieve the ratio [DBCO]/[N$_3$]=1. Before measurement, the solution of the polyisocyanide copolymer and a solution of the long crosslinker or the short crosslinker were mixed on ice in a 1:1 ratio, briefly homogenized and immediately heated to 37° C., for 1 hour, in a TA Instruments Discovery Hybrid Rheometer. After this, the gel was cooled down to 5° C. and was allowed to stabilize for 10 minutes. A gel with a storage modulus of 161 Pa was obtained at 37° C. The storage modulus at 5° C. was 95 Pa. The conversion of DBCO after 15 minutes was 81±10% (measured using UV-Vis). R=59%. Crosslink density=34 μM.

Example 2

Stability of the Crosslinked Hydrogel

Example 1 was repeated except that the samples were allowed to stabilize for 19 hours instead of 10 minutes at 5° C. The storage modulus of this sample after 10 minutes at 5° C. was 103 Pa (R=63%), and the storage modulus after 19 hours was 101 Pa (R=64%, Crosslink density=32 µM).

Experiment 3

Low Crosslinker Concentration Gives Loose Bundles

Example 1 was repeated except that the ratio [DBCO]/[$N_3$] was 0.5 instead of 1.0. The storage modulus of this gel at 37° C. was 185 Pa, and the storage modulus at 5° C. was 55 Pa. The conversion of DBCO after 15 minutes was 94±10% (measured using UV-Vis). R=30% Crosslink density=12 µM.

Experiment 4

High Crosslinker Concentration Gives Loose Bundles

Example 1 was repeated except that the ratio [DBCO]/[$N_3$] was 2.0 instead of 1.0. The storage modulus of the gel at 37° C. was 156 Pa, and the storage modulus at 5° C. was 31 Pa. The conversion of DBCO after 15 minutes was 63±10% (measured using UV-Vis). R=20%, Crosslink density=13 µM.

Example 5

Higher Crosslinking Temperature

Example 1 was repeated except that the crosslinking temperature was 50° C. instead of 37° C. The storage modulus of the gel at 50° C. was 478 Pa, and the storage modulus at 5° C. was 218 Pa. R=46%. Crosslink density not experimentally determined. Estimated (considering 90 reaction yield): 34 µM.

Example 6

Lower Crosslinking Temperature

Example 1 was repeated except that the crosslinking temperature was 25° C. instead of 37° C. The storage modulus of the gel at 25° C. was 48 Pa, and the storage modulus at 5° C. was 31 Pa. R=65%. Crosslink density not experimentally determined. Estimated (considering 90 reaction yield): 34 µM.

Experiment 7

Longer Crosslinker

Example 1 was repeated except that the long crosslinker, dissolved as 2 mg mL$^{-1}$ in milliQ, was used (6-10 nm instead of 3 nm). The storage modulus of the gel at 37° C. was 125 Pa, and the storage modulus at 5° C. was 40 Pa. The conversion of DBCO after 15 minutes was 89±10% (measured using UV-Vis). R=32%. Crosslink density not experimentally determined. Estimated (considering 90 reaction yield): 34 µM.

Experiment 8

Too Low Crosslinker Concentration Disintegrated Gel

Example 1 was repeated except that the ratio [DBCO]/[$N_3$] was 0.1 instead of 1.0. The storage modulus of the gel at 37° C. was 155 Pa, and the storage modulus at 5° C. was 2 Pa. The concentration of DBCO was too low to measure conversion using UV-Vis measurements. R<1%, Crosslink density=0.3 µM.

Experiment 9

Too High Crosslinker Concentration Disintegrated Gel

Example 1 was repeated except that the ratio [DBCO]/[$N_3$] was 10 instead of 1.0. The storage modulus of the gel at 37° C. was 260 Pa, and the storage modulus at 5° C. was 0.3 Pa. The concentration of DBCO was too low to measure conversion using UV-Vis measurements. R<1%, Crosslink density=0.3 µM.

Experiment 10

No Crosslinker

Example 1 was repeated except that no crosslinker was used. The storage modulus of the gel at 37° C. was 160 Pa, and the storage modulus at 5° C. was 0.6 Pa. R=0.4%. Crosslink density=0 µM.

Experiment 11

Random Crosslinking of the PIC Polymers, Not in the Bundles

Example 1 was repeated, except that the hydrogel was not heated 37° C. after homogenisation of the components, but kept at 5° C. to allow the crosslinking reaction to complete. After 2 hrs, the modulus stabilised at 7 Pa, indicative of a very weak gel. Crosslink density (but not in the bundles) estimated at 34 µM.

Experiment 12

Random Crosslinking of the PIC Polymers, Not in the Bundles

Example 1 was repeated, but in the presence of 1 M NaI, which increases the LCST of the PIC polymer. After homogenisation of the components, the sample was heated to 25° C. (below the LCST) to allow the crosslinking reaction to complete. After 2 hrs, the modulus stabilised at below 1 Pa, indicative of a very weak gel. Crosslink density (but not in the bundles) estimated at 34 µM.

What is claimed is:
1. A polymer hydrogel comprising:
   a) a polymer formed by the crosslinking reaction of a polymeric unit A according to formula (I), polymer A with a crosslinking unit B according to formula (II)

crosslinker B b) and water,
wherein
n=100-10,000;
m=independently;
FG is a functional moiety that can be covalently coupled to the complementary functional moiety F1 or F2 of the crosslinking unit (B);
wherein functional groups F1, F2, F and functional groups FG that can give covalent couplings are independently selected from alkyne-azide coupling, dibenzocyclooctyne-azide coupling, bicyclo[6.1.0]non-4-yne-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages, tetrazine-trans-cyclooctene coupling and NHS-ester (N-hydroxysuccinimide ester)-amine coupling;
k=0.01-0.05;
h=0, 1 or 2;
the spacer is an organic moiety, having a main chain comprising at least two functional moieties F1 and F2, wherein the length of the crosslinker in the extended conformation as determined by molecular modeling (including the spacer and the functional groups F1 and F2) is between 2.5 and 12 nm, or wherein the length is between 20 and 80 atoms.

2. The polymer hydrogel according to claim 1, wherein the amount of the polymer in the hydrogel ranges between 0.01 wt. % and 1 wt %, wherein the amount of water in the hydrogel ranges between 90 and 99.99 wt. % relative to the total weight of the hydrogel.

3. The polymer hydrogel according to claim 1, wherein the concentration of the functional groups FG ranges between 20-200 μM.

4. The polymer hydrogel according to claim 1, wherein the molar ratio between the functional group FG and the functional groups F1, F2, and F ranges between 0.5:1 and 2:1.

5. The polymer hydrogel according to claim 1, wherein each m is 3 or 4.

6. The polymer hydrogel according to claim 1, wherein k ranges between 0.02 and 0.04.

7. The polymer hydrogel according to claim 1, wherein the couplings are based on azide-alkene and/or azide-alkyn coupling.

8. The polymer hydrogel according to claim 1, wherein the functional groups F1 and F2 of the crosslinking unit are selected from and their derivatives.

9. The polymer hydrogel according to claim 1, wherein the spacer comprises polyethylene glycol units, having from 3 to 26 ethylene glycol units.

10. The polymer hydrogel according to claim 1, wherein the spacer comprises a short peptide sequence, that is a cleavable metalloproteinase (MMP), VPMSMRG, VPMSMRGG, RPMSMR, IPESLRAG, IPVSLRSG, VPLSLYSG, VPMSMR, PAYYTA, GPQGIWGQ, SGES-PAYYTA, GPQGIAGQ, RPFSMIMG, VPLSLTMG, YAAPVRGG, GTAGLIGQ or GDQGIAGF, wherein V=Valine; P=Proline; M=Methionine; S=Serine; R=Arginine; G=Glycine; I=Isoleucine; E=Glutamic Acid; L=Leucine; A=Alanine; Y=Tyrosine; Q=Glutamine; K=lysine and F=Phenylalanine.

11. The polymer hydrogel according to claim 1, wherein the crosslinking unit B is defined by any one of formulas IX-XII

IX

X p = 0-14

XI p = 0-14
Y = independently O or NH

XII p + q = 0-14
Y = independently O or NH wherein Φ is a photocleavabe dye that, as a result of the photochemical reaction, cleaves the spacer.

12. The polymer hydrogel according to claim 1, wherein the hydrogel has a R value of at least 40%, wherein R is defined as the percentage of stiffness remaining at 5° C., $G'_5$, as compared to the stiffness at the 37° C., $G'_{37}$:

$$R = 100\% \times G'_5/G'_{37}.$$

13. A process for preparing the polymer hydrogel according to claim 1, comprising the steps of:

a. copolymerizing a first comonomer of an oligo(ethylene glycol) functionalized isocyanopeptide grafted with a functional group FG and a second comonomer of a non-grafted oligo(ethylene glycol) functionalized isocyanopeptide, wherein the molar ratio between the first comonomer and the second comonomer is 1:100 and 1:20 to prepare a polymer (A);

b. dissolving polymer (A) in water to a concentration between 0.01 and 1 wt % polymer between 0 and 10° C. to prevent hydrogel formation;

c. adding a crosslinking compound having a spacer unit and at least two functional groups F (=F1=F2=(F)$_n$) capable of reacting with the functional group FG,
    wherein the functional group FG and the functional group F are chosen to react and form a coupling, wherein the coupling is independently selected from the group consisting of alkyne-azide coupling, dibenzocyclooctyne-azide coupling, oxanorbornadiene-based-azide couplings, vinylsulphone-thiol coupling, maleimide-thiol coupling, methyl methacrylate-thiol coupling, ether coupling, thioether coupling, biotin-strepavidin coupling, amine-carboxylic acid resulting in amides linkages, alcohol-carboxylic acid coupling resulting in esters linkages, tetrazine-trans-cyclooctene and NHS-Ester (N-Hydroxysuccinimide ester)-amine coupling;
d. bringing the hydrogel within 10 minutes to the desired crosslinking temperature for gel formation (fast) at temperatures above the LOST or gelation temperature and the reaction with a crosslinking compound (slower).

14. The process according to claim 13, wherein the temperature of reaction ranges between 20 and 50° C.

15. Cell cultures, comprising: cells, cell culture medium and the hydrogel according to claim 1.

16. The polymer hydrogel according to claim 11, wherein the number of ethylene glycol units (m) ranges independently between 2 and 10.

17. The polymer hydrogel according to claim 16, wherein k ranges between 0.02 and 0.04.

18. The polymer hydrogel according to claim 17, wherein the amount of polymer in the hydrogel ranges between 0.01 wt. % and 1 wt. %, wherein the amount of water in the hydrogel ranges between 90 and 99.99 wt. % relative to the total of the hydrogel.

19. The polymer hydrogel according to claim 11, wherein the concentration of functional groups FG ([FG]) ranges between 20-200 μM.

* * * * *